United States Patent

Alexander et al.

[11] Patent Number: 5,814,731
[45] Date of Patent: Sep. 29, 1998

[54] ULTRASONIC SCANNING APPARATUS FOR NONDESTRUCTIVE SITE CHARACTERIZATION OF STRUCTURES USING A PLANAR BASED ACOUSTIC TRANSMITTER AND RECEIVER IN A ROLLING POND

[76] Inventors: Alton Michel Alexander, 5550 Fisher Ferry Rd., Vicksburg, Miss. 39180; Richard Wayne Haskin, 1325 Wright Rd., Raymond, Miss. 39154; Dan Edward Wilson, 2659 Jeff Davis Rd., Vicksburg, Miss. 39180

[21] Appl. No.: 789,888
[22] Filed: Jan. 28, 1997
[51] Int. Cl.$^6$ ................................. G01N 29/28
[52] U.S. Cl. ................ 73/644; 73/624; 73/627; 73/635
[58] Field of Search ............... 73/635, 598, 600, 73/618–623, 627, 624, 628, 632, 633, 644

[56] References Cited

U.S. PATENT DOCUMENTS

| | | | |
|---|---|---|---|
| 3,616,682 | 11/1971 | Golis et al. | 73/600 |
| 4,088,028 | 5/1978 | Hildebrandt | 73/611 |
| 4,519,251 | 5/1985 | Dickson | 73/639 |
| 4,559,825 | 12/1985 | Martens | 73/622 |
| 4,615,218 | 10/1986 | Pagano | 73/639 |
| 5,062,301 | 11/1991 | Aleshin et al. | 73/635 |
| 5,404,755 | 4/1995 | Olson et al. | 73/639 |
| 5,549,004 | 8/1996 | Nugent | 73/640 |

FOREIGN PATENT DOCUMENTS 1438935  6/1976  United Kingdom ............ 73/635

*Primary Examiner*—Hezron E. Williams
*Assistant Examiner*—Nashmiya Fayyaz
*Attorney, Agent, or Firm*—Luther A. Marsh

[57] ABSTRACT

The invention is a carriage type sonic or ultrasonic testing apparatus for flaw and deterioration detection testing in a structure, especially concrete. The apparatus detects both location and type of flaw in a structure. The carriage unit incorporates a rolling pond feature which includes: i) foam-covered tracks and rollers, this soft foam material in addition to its primary function prevents vibration of the transducers while traversing rough surfaces such as weathered concrete. The tracks and rollers form a water-tight seal with each other and the specimen surface; ii) an air-removal brush assembly which maintains contact with a specimen surface to facilitate transmission and reception of ultrasonic energy into and out of a test specimen; iii) an ultrasonic isolator element and optional wave absorbers; and iv) the ultrasonic transducer suspension system. A transducer water bed is continuously maintained while the system is in motion across the concrete. A sealed space surrounds the transducer system, and that space is continuously flooded with water so as to keep the bottom sections of the transducers submerged. This sealed space continuously transports a sufficient amount of fluid (water) along the concrete surface for proper acoustic coupling. The ultrasonic transducer includes a granite wedge as an impedance-matching transducer faceplate material for concrete structural examinations.

15 Claims, 6 Drawing Sheets

5,814,731

ULTRASONIC SCANNING APPARATUS FOR NONDESTRUCTIVE SITE CHARACTERIZATION OF STRUCTURES USING A PLANAR BASED ACOUSTIC TRANSMITTER AND RECEIVER IN A ROLLING POND

STATEMENT OF GOVERNMENT INTEREST

The invention described herein may be manufactured and used by or for the United States Government for governmental purposes without the payment of any royalties thereon.

FIELD OF THE INVENTION

The invention pertains to an apparatus for nondestructive flaw and deterioration testing within a structure for detection of location and type therein using an ultrasonic transducer. The apparatus is an ultrasonic testing device with scanning capability particularly suited for testing solid concrete structures.

BACKGROUND OF THE INVENTION

A survey was conducted by the University of Nebraska in 1994 to determine what type of nondestructive techniques the states in the U.S. with departments of transportation use to test for delamination in concrete bridge decks. It was determined of the 50 states, 47 use the chain drag and hammer technique, which is an ASTM standard to map the presence and extent of delamination. Two states that do not survey are Hawaii and Alaska; Florida's bridges do not encounter the problem of delamination in their decks. A few states have experimented with infrared and radar but these techniques have limited test value and suffer from low resolutions. Concrete bridge decks are routinely subjected to a variety of detrimental environmental attack mechanisms. As a result, there are presently about 200,000 bridge decks in the U.S. that are in need of repair or replacement. The normal repair procedures are overlays or removal and replacement of the bridge deck. Both procedures are very intensive and disrupt traffic flow for extended periods of time. By developing devices and methods for evaluating existing bridge decks, significant repair cost savings could be realized with less down time.

Present methods of testing a concrete structure such as bridge decks include: i) laboratory tests on concrete samples taken from drilled cores in the structure that are often used to determine the condition thereof. Even though the removed concrete volume is later filled with new concrete, the structure is weakened from this type of destructive test method. Also, the aesthetic are disturbed from destructive testing. Core testing is a localized method of testing that will only provide information on the specific location from which the core is taken, thus providing an inaccurate overall assessment of the entire structure's condition; ii) manual acoustic methods that include the chain drag which is performed in accordance with standard ASTM D 4580 and the hammer technique, both are based on the human auditory discrimination of sound differences between solid and delaminated concrete. Problems associated with these two manual methods include human subjective interpretations that are not reliable since observations are usually affected by external noise and is a function of the operator's ability to discern pitch; iii) resonance-based methods used in commercially available devices that operate in a sonic range for determining flaw detection in concrete. Limitations of this type of techniques include limited measurement resolution when compared to UPE testing methods due to the fact that higher acoustic frequency is being used; iv) ground penetrating radar systems is yet another method currently used but does not provide sufficiently accurate indications of the structure's physical condition. This is due to acoustic energy being very sensitive to an air interface in concrete whereas electromagnetic energy is not. A ground penetrating radar system that encounters steel is highly reflective of electromagnetic energy and can mask the detection of reflected signals from flaws in reinforced concrete; and v) thermographic systems require consistent thermal loading of the concrete structure and are only capable of detecting large flaws. This type of test system is also limited in that it is sensitive to surface properties such as texture and color.

Although ultrasonic through-transmission systems have been used to evaluate concrete for several decades and are available commercially, ultrasonic pulse-echo (UPE) systems have not effectively been developed for such use. The ultrasonic standard method for evaluating concrete structures is ASTM C 597, "Pulse Velocity through Concrete". It is a pulse method that operates in a through-transmission mode. This technique requires both sides of the structure be accessible. Another standard method of concrete is resonant frequency test ASTM C 215:"Fundamental Transverse, Longitudinal, & Torsional Frequencies of Concrete Specimens". This method has limited utility for measurements since it is dependent on specimen shape and size. It operates primarily in the sonic range of frequencies (<20 kHz) and rarely operates above 20 kHz which is the case for a short specimen that is less than 5 inches in length. Note that this method is commonly referred to as the resonance method, but the resonance system developed by Mary Sanszlone and Nick Carino is referred to as impact-echo.

Through-transmission versus pulse-echo systems: There are significant differences between through-transmission systems and pulse-echo systems. Through-transmission systems are narrow-band systems using high-Q transducers while pulse-echo systems are wide-band systems using low-Q transducers. Through-transmission systems commonly use a point source to introduce the acoustic energy into the material rather than a piston source. A point source produces a spherical wave front while a piston source produces a plane wave front. A through-transmission system has a small area transducer point source, with respect to the wavelength while a pulse-echo system has a large area transducer, piston source with respect to that wavelength. With through-transmission systems, the pulse length can be large (numerous cycles) with respect to the distance between the opposite surfaces while for pulse-echo systems, the pulse length must be short (few cycles) with respect to the distance between the opposite surfaces. In summary, an optimum through-transmission system has a different transducer construction than an optimum pulse-echo system as discussed in the report by Alexander, A. Michel and Thornton, H. T. "Developments in Ultrasonic Pitch-Catch and Pulse-Echo for Measurements in Concrete", Presented at the American Concrete Institute (ACI) Convention, San Antonio, Tex., March 1987, ACI Special Publication SP-112in 1988. which provides the history of ultrasonic pulse-echo developments for concrete applications. An example of such an ultrasonic pulse-echo system for concrete testing applications includes U.S. Pat. No. 3,616,682 by McGolis et al. entitled "Ultrasonic Nondestructive Thickness Gauge."Limitations of this system include: i) the transducer is extremely large and heavy, i.e. a concrete surface must be flattened with a surface grinder; ii) this system performs only static measurements; iii) this system exhibits a low signal-to-noise ratio due to resonance occurring in the whole transducer where poor isolation occurs between the transmitter and receiver without acoustical matching into a concrete surface; and iv) this system cannot be used in a fluid for enhanced acoustic coupling since the receiver is not waterproof; v) the transducer suffers from a longer near-field distance due to large surface area.

Pulse-Echo versus Resonant-Frequency Echo Phenomena: There are also significant differences between resonant frequency wave-echo phenomena and pulse-echo phenomena as discussed in the report by Alexander A. M. in "Resonant-Frequency and Pulse-Echo Measurements," International Advances in Nondestructive Testing, Volume 16, pp. 193–215, 1991. A pulse is a burst of acoustic energy existing for a time which is very short as compared with the two-way travel time (time for pulse to travel from surface to flaw or backwall and return to surface) in a specimen. Resonant frequency energy exists for much longer in time than the energy from a pulse and is equal to the time required for the energy to make numerous round trips of the two-way travel time in the specimen. Also it is known that the wave velocity is not equal to the pulse velocity in the same concrete specimen.

P-wave velocities calculated by the impact-echo method (resonant frequency method) are approximately 10 percent slower than the velocities determined by the pulse velocity method, see the report Nicholas J. Carino and Mary Sansalone "Impact-Echo: A Method for Flaw Detection in Concrete using Transient Stress Waves", Report No. NBSIR 86-3452, National Bureau of Standards, Washington, D.C., /PB87-10444/AS, National Technical Information Service, Springfield, (September 1986), p.137.

When making resonant frequency wave-echo measurements, one is measuring the frequency of oscillations of standing waves reflecting back and forth between the top surface of the material and the backwall or flaw from the material. When making pulse-echo measurements, the leading edge of the pulse's time-of-arrival is measured, and no standing waves exist since the frequency components of a pulse are too high to excite resonance. For resonant frequency testing, the local frequency is in the audio range, whereas in pulse testing, the frequency is typically in the ultrasonic range. For longitudinal resonant frequency testing, the wavelength is twice the thickness of the specimen. For pulse-echo testing, the wavelength is only a fraction of the dimensions of that specimen thickness. For resonant frequency testing the wave velocity is a function of the size and shape of the specimen. For pulse-echo testing, the velocity is a constant for different sizes and shapes. In summary, the phenomena are widely different for resonant frequency testing than for pulse-echo testing and hence the equipment for making measurements is significantly different for each technique.

Moreover, UPE systems have found an important place in the various industries for evaluating the type and magnitude of defects in homogeneous materials. The automotive and aerospace industries are two examples. UPE systems are also needed in the construction industry and especially for diagnosing the condition of concrete structures. However, concrete is a heterogeneous material and UPE systems used for homogeneous materials normally cannot be adapted to work for concrete. A laboratory system capable of dealing with nonhomogeneous materials was developed in the late 1980's for making ultrasonic pulse-echo measurements in concrete, see the report by Thornton, H. T. and Alexander, A. M. "Repair, Evaluation, Maintenance, and Rehabilitation Research Program, Development of Nondestructive Testing Systems for In Situ Evaluation of Concrete Structures," WES TR REMR-CS-10, December 1987. The U.S. Army Corps of Engineers Waterways Experimental Station in Vicksburg Mississippi, developed a UPE prototype system for defect and deterioration detection of concrete. Although the hardware performed satisfactorily, the system was not user friendly and required highly trained personnel to both operate this system and interpret observed data. This UPE system was heavy, bulky, and complicated to use. Also, for difficult interpretations, the analysis of signals had to be performed by the computer. The invention herein is field ready that can be operated by semi-skilled personnel since it is integrated for performing on-site real-time testing.

Acoustical testing devices and methods provide a better testing approach for assessing the condition of concrete. An example of this includes the teachings in U.S. Pat. No. 5,404,755 by Olson et al. entitled "Scanning Apparatus and Method for Non-Destructive Materials Evaluation and Mapping Through Use of Acoustic Waves", which is incorporated by reference. This teaching discloses an apparatus for nondestructive testing of structures by acoustic signals transmitted from a carriage unit. The carriage includes a frame which is wheel mounted to move over the surface of the test candidate. An internally-mounted piezoelectric crystal roller is used as an acoustic signal generator or receiver that is suspended from the carriage with two degrees of spring freedom to allow accommodation of irregularities in the test candidate surface. The assembly including the piezoelectric crystal roller and its flexible mounting are configured as a replaceable module relative to the carriage frame. The same carriage is suitable as an echo type acoustic scanner or, in combination with other devices or carriages. This device can be used for detecting or generating compression, shear or surface waves in a test specimen.

Limitations of this teaching compared to the instant invention include: i) the Olson carriage system is not suitable for making UPE measurements which is made by the instant invention transducer floating pond concept. These acoustical characteristics are very important when making measurements of an inhomogeneous material such as concrete. The instant invention transducer elements generates an acoustical beam whose rays of energy are semi-collimated, with a narrow beam width relative to a point source. These collimated rays can be directed into a test specimen by use of a wedge, to produce reflections which arrive at the receiver. This is accomplished by acoustic coupling between the flat transducers with large area and the specimen's surface and by angled face plates. Also, the instant invention reduces Raleigh surface wave interference by means of a large transducer receiving area. The large receiving area spatially averages incident surface wave energy and reduces its detrimental masking effect of the desired longitudinal echoes. ii) The Olson carriage system is only capable of coupling to a material at a point or down a narrow line only when placed on a smooth surface. The Olson system if used in real world applications would encounter rough surfaces which normally occurs on weathered and deteriorated concrete structures resulting in only point coupling. This in turn would generate an undirected sound beam with a spherical wave front. In contrast, the instant invention's use of a piezoelectric material with a low planar coefficient reduces transverse energy transmission and reception in the transducers which improves signal detection by reducing interference. This piezoelectric material improves the ability to generate and receive pulses normal to the faceplate of the transducer whose wave front is approximately plane. Also, the instant invention's transducers do not rotate or make contact with a specimen surface which allows for use on rough surfaces without modification whereas the Olson carriage requires much larger than normal transducer diameters as the surface roughness increases. Moreover, mechanical failure and component wear by the instant invention is reduced since the transducers do not require rotation or surface contact. iii) The Olson carriage system does not allow for acoustically coupling a transducer of arbitrary area to a test specimen as in by the instant invention. Also, the use of large area transducers for acoustical reception as by the instant invention reduces scattering effects from inhomogeneous materials and increases the a transducer's sensitivity to deep reflections in the interior of the material structure which are also accomplished by spatial averaging. iv) The Olson device, the use of a fluid is optionally used for coupling enhancement with the primary coupling means being direct contact between the transducer and the material surface. This fluid used on the test specimen surface is not confined, the coupling fluid depth is limited to a thickness created by the surface tension property of the fluid and the properties of the specimen surface which can prevent optimum acoustic coupling between a transducer transmitter and receiver. In contrast, the instant invention's carriage assembly includes components for transporting a layer of coupling fluid across the test specimen surface referred to below as the rolling pond is necessary for the instant invention. v) The Olson carriage system primarily operates in the sonic range. The instant invention's ultrasonic scanning carriage primarily operates in the ultrasonic range which is an order of magnitude higher than Olsen's system. The wavelength used in the Olson system is an order of magnitude greater than the wavelength of the instant invention, hence the instant invention's scanner resolution exhibits an order of magnitude greater compared to an based Olson system. In concrete, the width of the sound beam of the instant invention diverges approximately 8 degrees off a normal in the far field (to the faceplate) while that of the Olson device is 90 degrees off the normal by definition of a point source. In an Olsen based system which uses such a wide angle, it is impossible to tell the location of a flaw in concrete specimen since a recorded echo does not necessarily originate from beneath the transducers. Echos from the instant invention primarily occur from beneath the transducer.

Accordingly, the present invention is an improvement over current known carriage devices with ultrasonic testing capabilities of a specimen by providing an improved acoustic coupling transducer unit suspended from a carriage for rapid data collection that can be analyzed efficiently by neural network processing algorithms, or by an experienced operator's examination of B-scan data.

SUMMARY OF THE INVENTION

The present invention pertains to a carriage type sonic or ultrasonic testing apparatus for flaw and deterioration detection testing in a structure. The apparatus detects both location and type of flaw in a structure using a nondestructive testing method which permits for a cost effective assessment and/or repair of a concrete structure when compared to destructive methods. The carriage unit incorporates a rolling pond feature which includes: i) foam-covered tracks and rollers, this soft foam material in addition to its primary function prevents vibration of the transducers while traversing rough surfaces such as weathered concrete. The tracks and rollers form a water-tight seal with each other and the specimen surface; ii) an air-removal brush assembly which maintains contact with a specimen surface to facilitate transmission and reception of ultrasonic energy into and out of a test specimen; iii) an ultrasonic isolator element and optional wave absorbers; and iv) the ultrasonic transducer suspension system. This method overcomes deficiencies inherent in current measurement systems, viz. the use of stationary measurements by transducers using a compliant coupling grease. This fluid-coupling method significantly improves measurement data acquisition speeds. A transducer water bed is continuously maintained while the system is in motion across the concrete. A sealed space surrounds the transducer system, and that space is continuously flooded with water so as to keep the bottom sections of the transducers submerged. This sealed space continuously transports a sufficient amount of fluid (water) along the concrete surface for proper acoustic coupling. The ultrasonic transducer includes a granite wedge as an impedance-matching transducer faceplate material for concrete structural examinations.

The ultrasonic transducer is made of a short flint (lead) glass plate with piezoelectric material attached thereto made of lead metaniobate piezoelectric ceramic. This material is ideally suited for concrete ultrasonic testing because it exhibits a both a low-Q and low planar coefficient. A preferred 200 kHz center frequency is selected because of the trade-off between penetration depth and resolution. Penetration depth is primarily a function of attenuation losses due to scattering and increases as frequency is reduced. Pulse resolution is a function of the pulse width and increases as frequency is increased. The piezoelectric elements are bonded in the shape of a rectangular mosaic and acoustically matched to a directing wedge. The rectangular mosaic creates a beam pattern in the concrete with a desired fan shape. An angular pitch provided by a wedge is preferable in the transducer design for examinations of concrete plate structures so that reflections are directed towards the receiving transducer. The receiving transducer is large in area to spatially average the reflected ultrasonic energy thereby reducing grain noise while enhancing reflected plane waves. The large receiving area also helps reduce noise from surface waves. This is accomplished because an arriving surface wave only affects a small portion of the receiver at any instant. For long cycles of surface waves which could occupy the entire receiver area, the averaging effect should limit magnitude response. This data can then be compiled and analyzed allowing the concrete structure's condition to be characterized from this output data that can be analyzed efficiently by a neural network data analyzing capability or an experienced human operator.

The transducers use acoustical matching techniques using a layered structure comprising: i) a low-Q piezoelectric ceramic elements attached to one side of ii) a short flint glass plate which in turn is attached to iii) a granite acoustic impedance matching wedge, yielding a broadband transducer. The acoustic impedance of the glass optimally, geometric mean, is between that of the piezoelectric material and the granite, and the granite's impedance is between that of the glass and concrete. This allows the ultrasonic scanning carriage to efficiently transmit and receive short pulses with little transducer ringing which is desirable when performing UPE measurements.

The primary purpose of the carriage assembly of the ultrasonic scanning carriage is to transport a layer of coupling fluid across the test specimen surface. The ultrasonic scanning carriage can operate underwater as well. Vibrational noise in a structure has not been observed to influence the high frequency operational characteristic of the ultrasonic pulse-echo system. The ultrasonic pulse-echo transducers exhibit low transverse response which reduces echo interference.

The ultrasonic scanning carriage can measure various types of civil engineering structures that include: floors, slabs, underwater walls, lock walls, dams, stilling basins, pavements, bridge decks, underwater columns, and beams. The ultrasonic scanning carriage is specifically designed to test concrete and masonry structures and be readily modified to test wood, metal, stone, composites, cast iron, austenitic metals (large grain) materials. The ultrasonic scanning carriage can detect problems in concrete with the following: corrosion of reinforcing steel, amount of concrete cover over reinforcement, position, and amount of steel reinforcement, internal cracking, lack of consolidation (honeycombing), foreign objects, delamination in bridge decks, voids beneath concrete foundations, thicknesses of layers, and micro cracks from alkali aggregate reaction, fire damage or freeze & thaw damage.

The transducers of the instant invention can perform UPE measurements in a stand alone stationary configuration. The low impedance of the thin layer of air between the transducer and concrete specimen requires that the air interface be replaced with some liquid compliant having a higher impedance than air; an impedance that more closely matches the transducer and concrete. The compliant is normally viscous, and care must be taken to rotate and press the transducer down on the compliant so as to squeeze the air from the compliant material after it is spread on the concrete surface by hand. This method of use is for specific locations under test.

Accordingly, several objects of the present invention are:

(a) To provide a more reliable and operationally cost effective carriage driven ultrasonic testing device that can be used to rapidly collect information of the internal structure of a solid member of a structure.

(b) To provide an ultrasonic scanning carriage that is more immune to external noise, collects data on a denser grid, collects data while moving and provide a computer test record.

(c) To provide an ultrasonic scanning carriage unit with an improved acoustic transducer which is an improved design over current designs for use with concrete plate structures due to expected backwall and flaw depths encountered in such structures.

(d) To provide an ultrasonic scanning carriage unit with transducer that allows for accurate data collection that can be outputted and analyzed efficiently by a neural network data analyzing processor unit or experienced operator; and (e) To provide an ultrasonic transducer device that allows for accurate data collection over a particular area of interest.

Still further advantages will become apparent from consideration of the ensuing detailed description.

DETAILED DESCRIPTION & OPERATION

Figure 1:
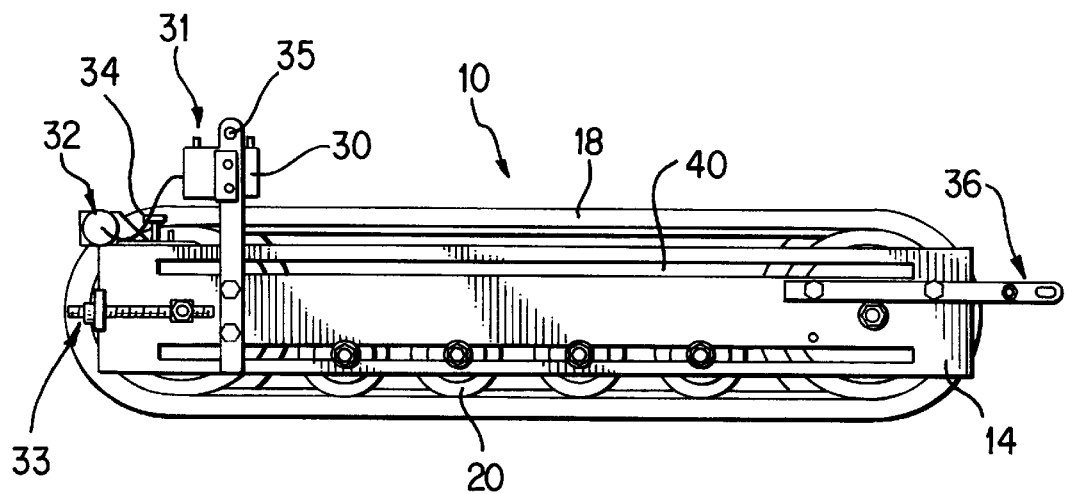
FIG. 1 shows a side view of the ultrasonic scanning carriage which uses ultrasonic waves between a symmetrical pair of transducers that act as transmitter and receiver.
Figure 2:
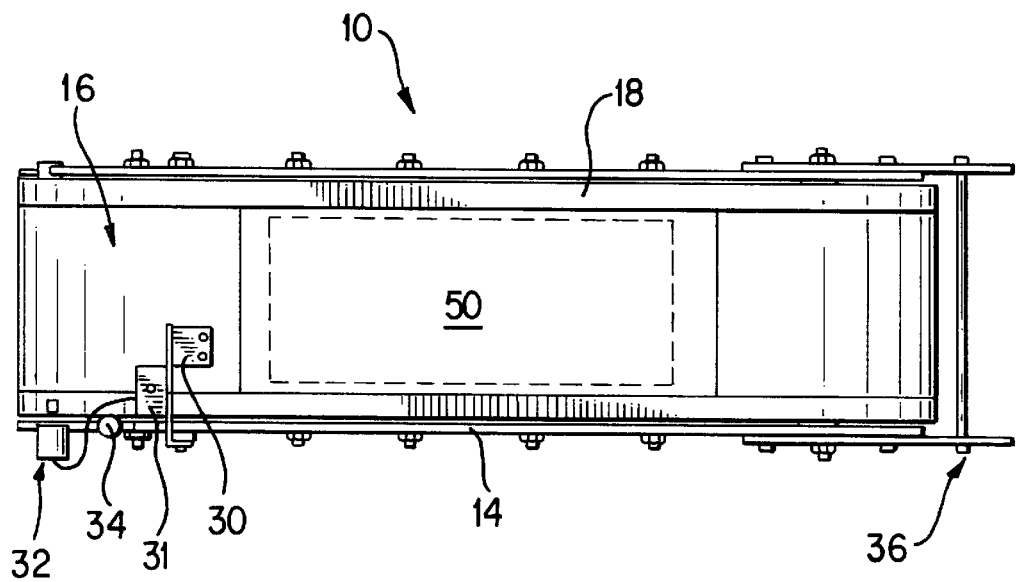
FIG. 2 shows a top view of the scanning carriage of FIG. 1
Figure 3:
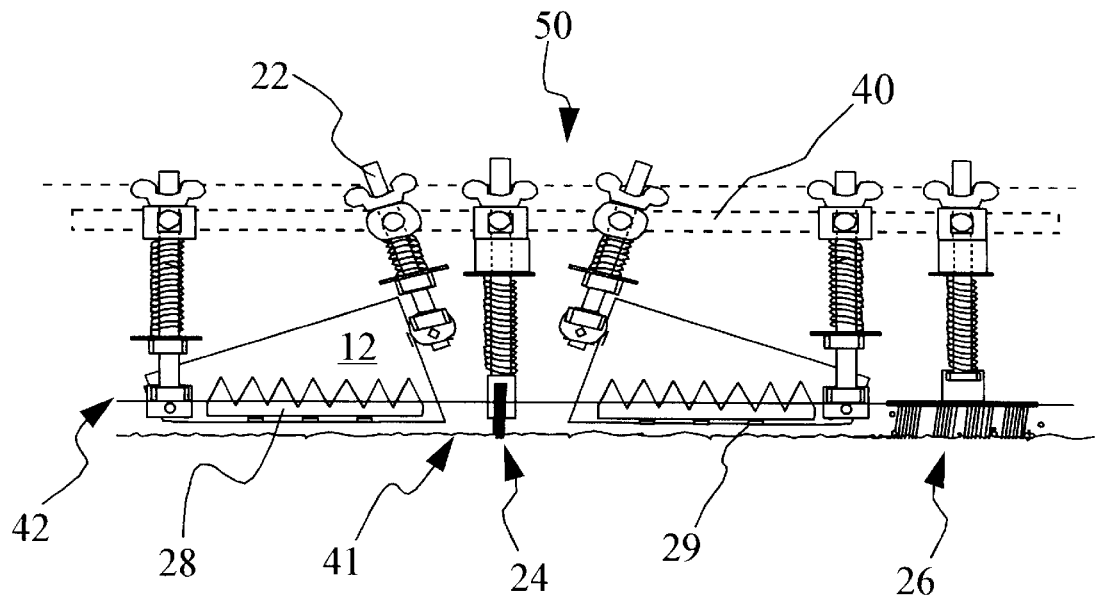
FIG. 3 shows a side view of components within the ultrasonic scanning carriage's support assembly for the transducers.
Figure 4:
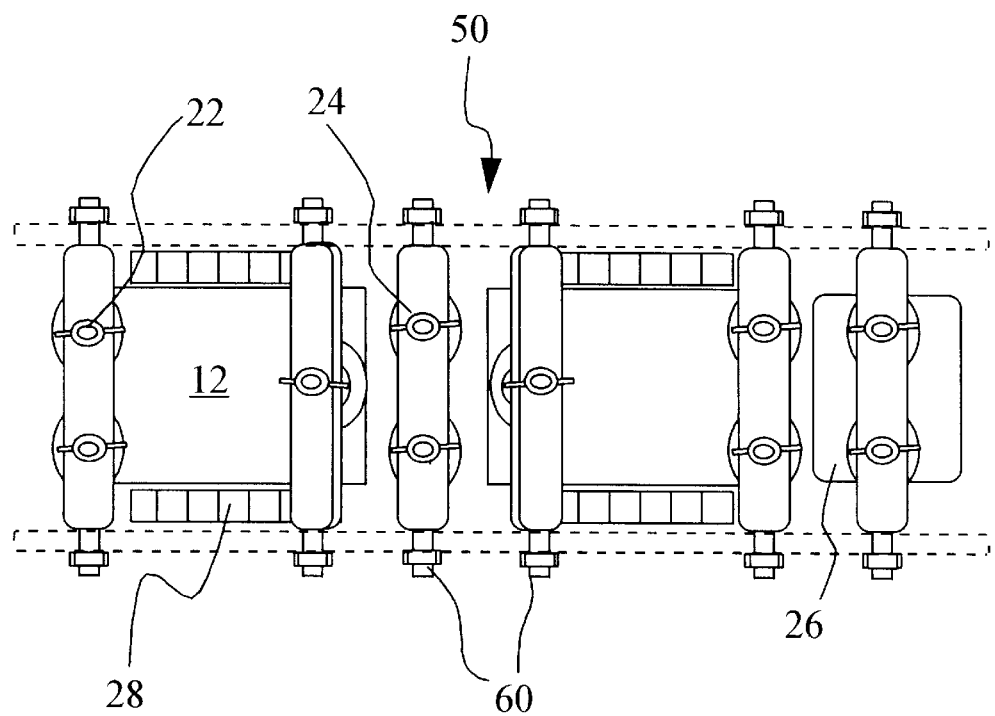
FIG. 4 shows a top view of FIG. 3.

FIGS. 1 and 2 shows the ultrasonic scanning carriage 10 which uses ultrasonic waves between the pair of transducers 12 in a pitch-catch mode operation which is used for flaw detection in solid structures. The carriage 10 includes a suspension assembly 50 of transducers 12 as shown in FIGS. 3 & 4. A unique wave coupling phenomenon between the pair of transducers 12 and the concrete surface 41 allows for accurate and high density real-time data collection capabilities during movement of the carriage 10 over the test specimen. Data output from the receiving transducer 12, which can be either unit 12 according to system configuration, outputs data to a processor unit with pattern recognition capabilities, viz. artificial neural network programing that can aid in the interpretation of scanned data. The processor can also include expert system programing that can automate the test procedure through using the invention's ultrasonic scanning carriage 10 or experienced operator examination of B-scan data.

The ultrasonic scanning carriage 10 includes a continuous rotary pulse encoder 32 in contact with one of a pair of soft moving belts 18 located on each side of the unit's rolling pond frame 14 to generate electrical pulses as the belts 18 moves across a structural surface. The thumbwheel 34 allows positioning of the encoder unit 32 so that the encoder and belt 18 contact pressure can be adjusted to prevent slippage or binding of these units. Alternatively, the belts 18 and cooperating encoder's 18 pulley may be cogged to prevent slippage. These pulses are counted digitally and then used to trigger and coordinate proper signal flow of the pair of transducer's 12 transmitter and receiver transducers 12 in an overall data acquisition system with a processing unit. This data position encoding system derived from data of the encoder 32 allows a user to set the desired separation distance of the ultrasonic readings. Data rates from a signal per foot up to twelve signals per inch are obtainable using the ultrasonic carriage 10. A small battery-powered amplifier 30 such as the Panametrics model 5660B, capable of 40 or 60 dB gain is used to amplify received ultrasonic signals from receiver transducer 12 for output to appropriate signal conditioning and analyzer devices. The amplifier 30 should be located near the receiver 12 to reduce electrical noise.

Mobility of the carriage 10 across a specimen surface can be accomplished by: i) manual towing of the carriage 10 with a winch and pulley setup using eyelet 36 for attachment of a cord to carriage 10; or ii) including an electric motor in carriage 10 that is mechanically coupled to the rollers 16.

The pulses generated by the encoder 32 as carriage 10 moves are counted by a presetable pulse counter 31. When a preset number of pulses are counted, a triggering pulse can be sent to a pulse generator and data acquisition system. An example of a pulse generator that can be used with carriage 10 is the VELONEX model 360 high power pulse generator. This pulser generates a short high voltage pulse which is sent to the transmitting transducer 12. The resulting mechanical forces in the test specimen are received by the receiving transducer which converts them into an electrical signal. This low voltage signal is amplified by 30 and sent to the data acquisition system, e.g. a Nicolet 430 oscilloscope. The data acquisition system which was triggered by the encoder at the same time the pulse generator was triggered digitizes the resulting electrical signal. Many of the data acquisition system properties are tied to the specific transducer characteristics, e.g. a transducer's center frequency and quality factor defines the minimum sample rate while signal amplitude defines a needed voltage digitization range. For specimen scanning, the data acquisition hardware can quickly collect and store many successive signals without buffer overflow or delaying the data acquisition process after receiving a trigger signal.

Figure 5:
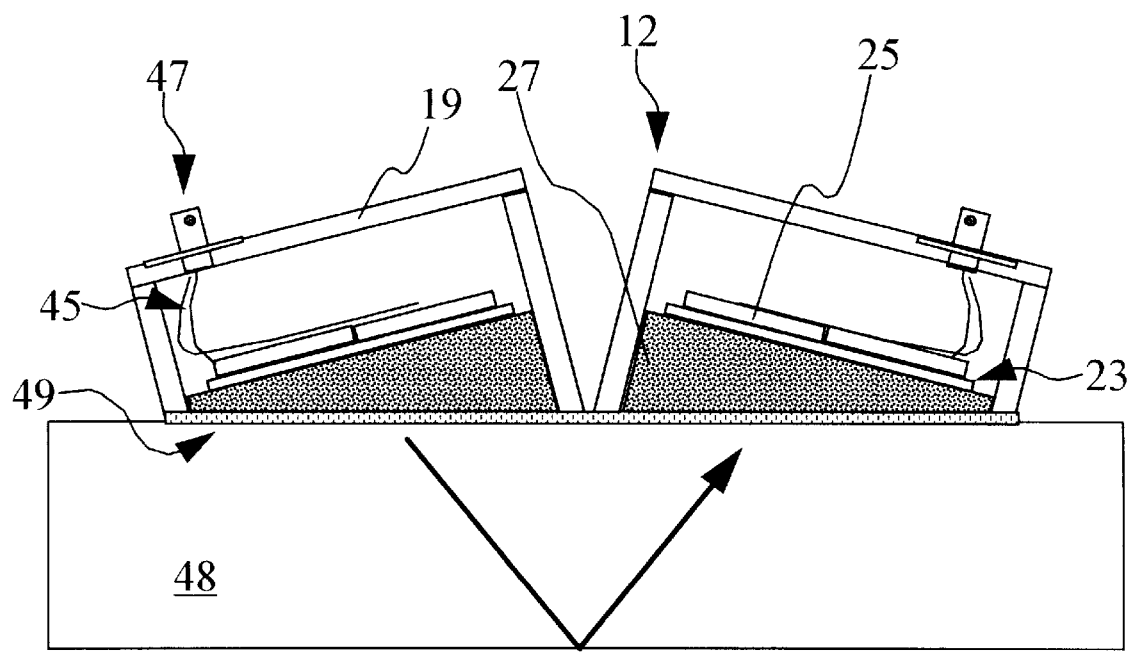
FIG. 5 shows a side view of the carriages ultrasonic transducer transmitter and receiver in relation to a specimen.
Figure 6:
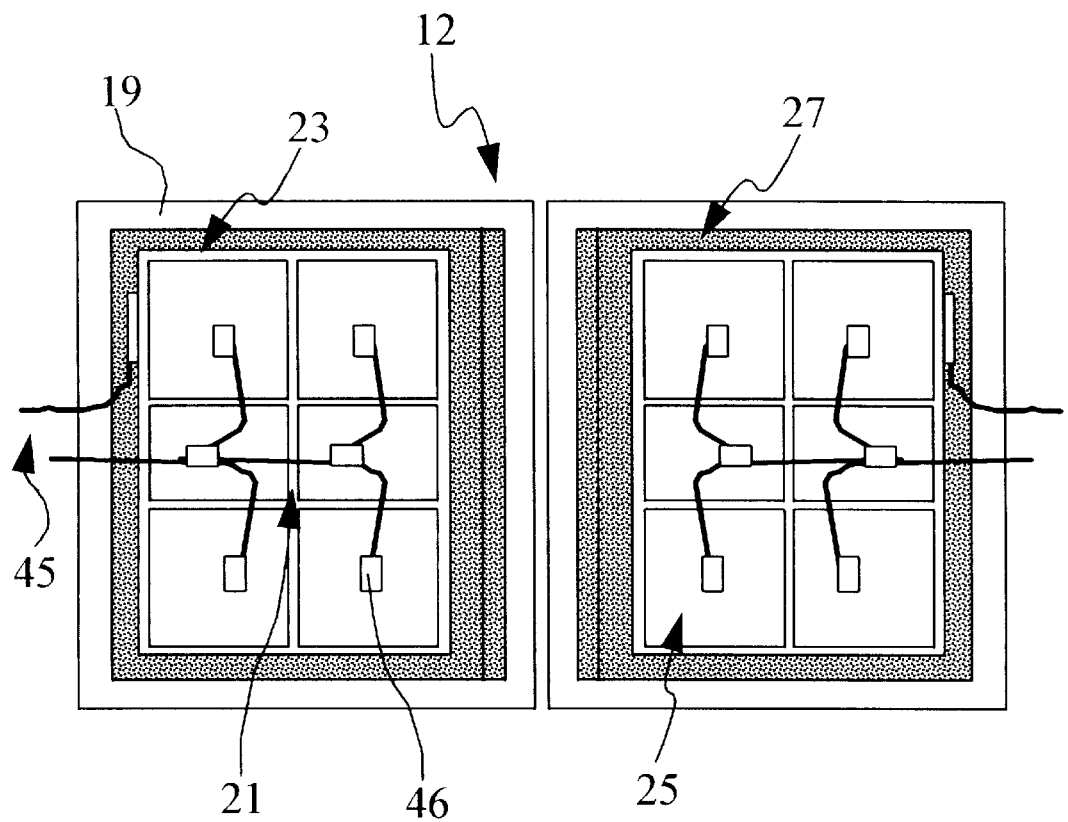
FIG. 6 shows a top view of FIG. 5.

Ultrasonic transducers 12 operate in an ultrasonic energy regime which is generated and received by lead metaniobate piezoelectric ceramics such as KZT-81 with a center frequency of 200-kHz and a quality factor of about 2. These ceramics are placed in a mosaic pattern design 21 to create a semi-collimated ultrasonic beam in the interior of the concrete specimen. FIGS. 5 and 6 show the transducers 12 construction that can be used in assembly 50. A short-flint glass plate 23 which optimally matches the piezoelectric ceramics 25 to a directing wedge faceplate. The glass plate 23 has an electrode 46 which consists of gold sputtered on the face to which the piezoelectric ceramics 25 are attached with a conductive epoxy. The electrodes 46 are attached to leads 45 that in turn can be attached to an electrical connector 47. Scotch weld epoxy is used to attach the opposite side of the glass 23 to a granite wedge 27 which directs ultrasonic energy from the pair of transducer's 12 transmitter towards the accompanying receiver. The wedge's acoustic impedance is between that of the glass and concrete and provides an acoustic match to the concrete. The wedge 27 is also quarter-wavelength matched under the ceramic centers and in the center of the transducer. The transducers 12 are encased in a protective waterproof covering material/closure 19 to protect them from adverse effects due to fluids in the rolling pond frame 14. The transducer enclosure 19 also isolates the transducers 12 from unwanted acoustical coupling in the fluid bath as well as the carriage assembly 50. The enclosure can be made of plexiglass encased in aluminum. The acoustical mismatch between the granite, plexiglass, aluminum and fluid bath facilitates this isolation. The transducer 12 as shown are designed for examinations of slab concrete of approximate 8–9 inch thickness. The glass plate 23 is about 5 mm in thickness and the planar constructed granite wedge 27 is about 13.5° with respect to the planar surface that attaches to the glass plate 23. This angle is reduced when designed for thinner concrete slabs to be tested. The depth offsets on the rectangular sides are approximately 0.4 inches and 1.5 inches.

Transducers 12 in a stand alone test mode as shown in FIG. 5 would use a layer of coupling grease 49 such as silicon or a coupling fluid placed between the test surface 48 and transducer 12. For thicker test specimens, the transducers 12 separation distance would be increased until an acceptable backwall echo was received. Test on thin specimens are satisfactorily performed with the transducers 12 close together. For performing flaw testing on a thick structure, the pair of transducers 12 transmitter can be left stationary while the receiver is placed at discrete separation distances. The separation distance should not exceed that needed for optimum backwall signal reception.

To modify the transducers 12 for other types of test specimens 48 other then concrete, acoustical properties and other physical properties such as surface 41 roughness and specimen thickness must be considered. In particular, the wedge 27 and quarter wavelength plate 23 is modified so as to acoustically match a new specimen's properties. Material tables with longitudinal velocity and acoustical properties would be used in selecting new materials for the wedge 27 and plate 23. Each matching wedge and plate layer is approximately the geometric mean, square root of the product, of the two adjoining materials. The plate's 23 matching thickness are determined by the material velocity and the transducer 12 center frequency. The frequency of transducers 12 operation would be changed according to the velocity and attenuation of specimen 48 to be examined. In general, higher velocity materials require higher transducer frequencies.

Variations to the transducer mosaic 21 size would be changed depending on the scattering properties, velocity, and expected maximum specimen 48 depth. In general, thick specimens with high attenuation need larger transducer 12 planar areas; increased heterogeneity of a specimen 48 requires larger transducer 12 areas to reduce grain-noise; higher velocity materials require larger transducer area for plane wave generation. The transducer 12 angle is determined by considering the matching properties of the wedge, the expected reflection depths, and the percentage of longitudinal and shear wave energy introduced at different incidence.

A fluid coupling system within the frame 14 is used to transport a layer of water 42 or other low viscous fluid across the surface 41 of the concrete under test. Soft closed-cell foam is used to form a watertight interface with the concrete surface and between the rollers 16 and belts 18. Silicon grease or a comparable substance can be spread on the insides of the belts where they contact the roller foam to improve the quality of the fluid seal between the belts 18 and the rollers 16. The pair of rollers 16 are formed by gluing soft closed-cell foam to the cylindrical surface of a rigid roller. The pair of belts 18 are fabricated by sputtering a layer of hot ethylene propylene diene (EPDM) rubber on two V-type fan belts followed by gluing a layer of soft closed-cell foam to the EPDM rubber. The weight of the frame 14 with transducers 12 is heavy enough such that an adequate sealing pressure is maintained between the unit 10 and the concrete surface 41. This heavy weight also helps seal the roller/belt interface at the specimen surface through increasing their contact pressure. This pressure increase is caused by deformation of the belts 18 and rollers 16. Multiple pulleys 20 located along the length of the belts help maintain a continuous fluid sealing force between the soft foam on belts 18 and the concrete surface. As the unit 10 is moved over the concrete, the front and back rollers 16 and the belts 18 on the side move on the concrete surface and against each other without slippage so that foam wear is minimal. When not in use the unit 10 can be lifted by eye hole 35 and be supported by blocks under the frame 14 so that the foam on the rollers 16 and belts 18 are not deformed by prolonged compression. The separation distance between the rollers 16 can be adjusted by tensioning assembly 33 so that the belt tension can be maintained. The frame 14 is slotted 40 at the top so that the transducers 12 and supporting components can be suspended at various positions in the fluid at the base of the frame 14 above the concrete surface 41. FIG. 3 & FIG. 4 show a side and top view of the support assembly 50 within the frame 14.

A spring-loaded fine-bristled brush 26 sweeps the concrete in front of the leading transducer 12 as the frame progresses across a concrete surface. This sweeping removes tiny air bubbles that are visible from the surface of the concrete. If these bubbles are not removed, sufficient ultrasonic energy cannot be transmitted into or received from the concrete surface. Because aged concrete is often porous, pre-wetting the surface in front of the rolling pond frame 14 is beneficial in reducing air pockets in the recesses within the concrete surface. This is due to the fluid having more time to soak into surface pores and being pressed in by the lead roller 16 of the carriage 10. The transducers 12 are suspended on spring-loaded threaded rods with wing-nuts 22. The wing-nuts on top of these rods allow for fine adjustment of both i) angle and ii) elevation of both transducers 12. The slots in the frame also allow for each of the transducers 12 separation distance to be adjustable. This adjustment capability is an important feature for optimizing wave amplitude and shape of received reflections to the transducers 12. The damping of the soft closed-cell foam on the rollers 16 and belts 18 that the ultrasonic scanning carriage 10 travels on helps reduce vibration to one of the transducers 12 when traveling over rough concrete surfaces. The transducers 12 attached to spring-loaded threaded rods with wing-nuts 22 are spring loaded so that the transducers 12 will lift up should they accidentally strike the concrete surface. The horizontal cross-frame supports 60 connects to the rods 22 and isolation component 24 of the assembly 50.

An isolation component formed from a spring-loaded closed cell foam strip 24 can also be used to block ultrasonic energy traveling from the transmitter to receiver transducers 12 through the fluid on the concrete surface 41. Another type of device that can be used to control ultrasonic reflections in the water are sponges 28 with wave-trapping geometry's. These sponges 28 supported by mounting arms 29 are placed in the water beside the transducers 12 to reduce the amplitude of reflected ultrasonic energy trapped in the fluid layer. These sponges 28 also help reduce slosh from acceleration of the fluid within the rolling pond frame 14. Excessive slosh creates low frequency noise in the received ultrasonic data.

Figure 11:
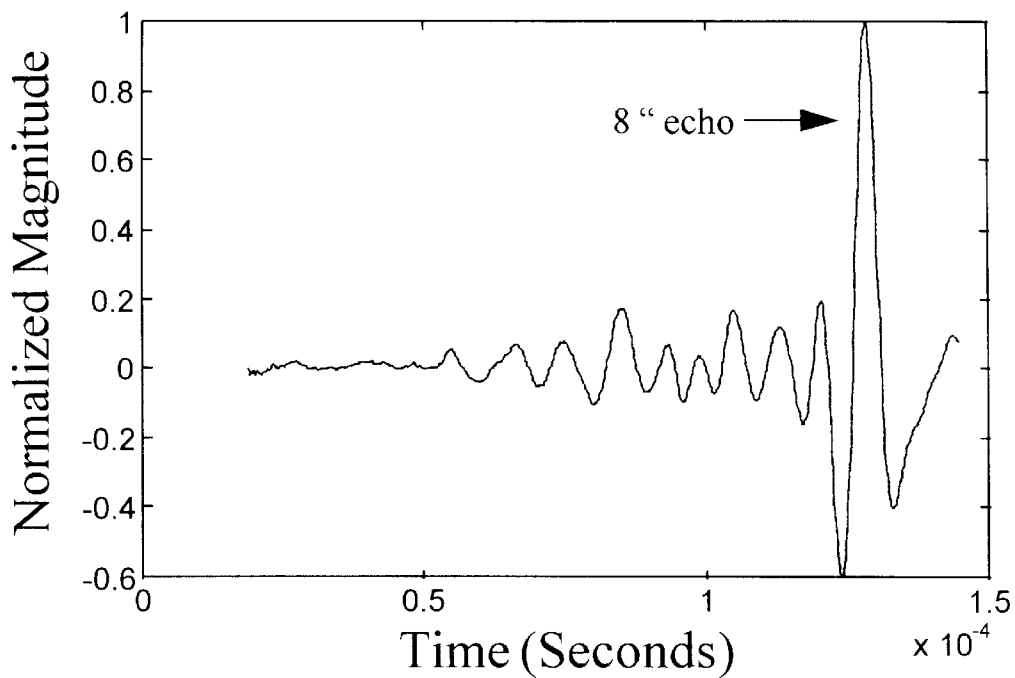
FIG. 11 shows an ultrasonic pulse-echo signal from an eight-inch thick concrete slab. The horizontal time axis is proportional to reflection depth.
Figure 12:
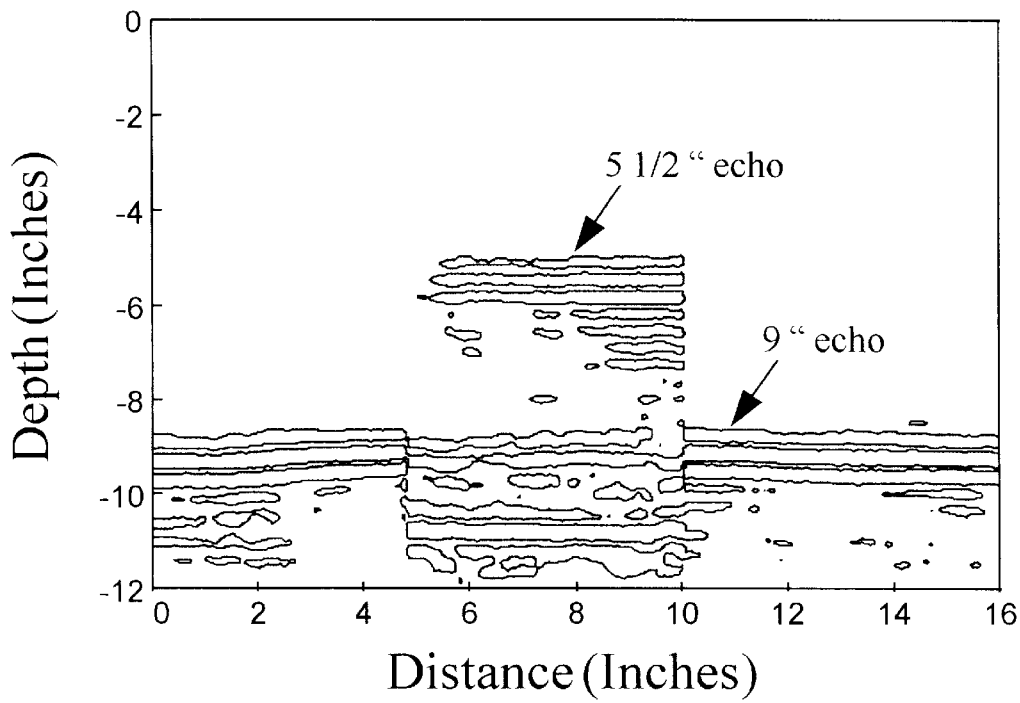
FIG. 12 shows a contour plot of scanned ultrasonic pulse-echo data from a nine-inch thick concrete slab.

Performing test on a concrete surfaces 41 include using the ultrasonic scanning carriage 10 on a thin solid slab such as a concrete floor or bridge deck. FIG. 11 shows an ultrasonic pulse-echo signal from an eight-inch thick concrete slab. The horizontal time axis is proportional to reflection depth. An ultrasonic reflection from a nine-inch thick concrete slab will appear as a large amplitude peak as shown in FIG. 12. For this type of test geometry, an operator can obtain reflections from the reinforcement and the backwall surface when a flawless section is scanned. Reflections from a reinforcing bar typically appears without masking these backwall reflections. When a flaw such as a delamination is encountered, the backwall echo disappears and a reflection at the flaw depth will show up instead. Scans are produced by normalizing reflected signals to create a matrix where each reflection is a column called a normalized B-scan.

Data acquisition and interpretation requires consideration be given to pulse time travel. Since the propagating pulse must pass through the quarter wavelength plate 23, wedge 27, and fluid layer 42, an estimation or calibration of the delay time in traveling though these materials is usually required. Their are many ways of finding these time delays. One method is to measure an echo time from a specimen 48 where the two-way travel time is already known. The additional delay from the transducers 12 and fluid layer 42 can then be found by subtracting the measured arrival time from the known two-way travel time.

Each of the transducer's 12 elevation should be set so that each transducer face nearest the concrete surface is as close as possible without making contact with the surface. Rougher more irregular surfaces may dictate greater elevation of the transducers. The transducer's 12 angles and separation distances are set so that reflections from the backwall face, up to the surface reinforcing layer, are obtainable. Short scans can be used to calibrate the velocity of concrete from the backwall echo. The various wave types of ultrasonic energy are complicated and there is an enormous amount of information in these backscattered reflections. Various signal processing techniques can be applied to the signals to derive certain characteristics. These characteristics are then used as inputs to a pattern recognition computer programming such as an artificial neural network that automatically interprets observed data or an experienced experienced operator can interpret B-scan data.

Figure 7:
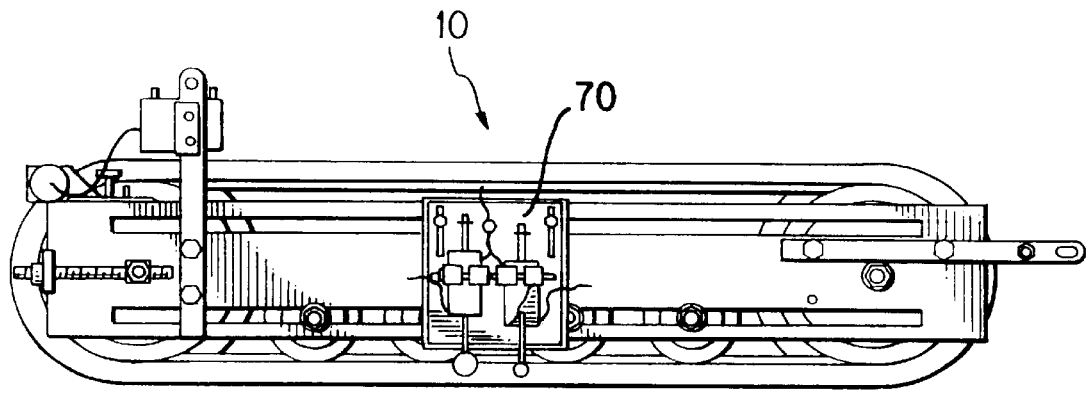
FIGS. 7 & 8 show a side and top view of the carriage with the additional optional feature of a solenoid impact device for performing impact-echo resonant testing.
Figure 8:
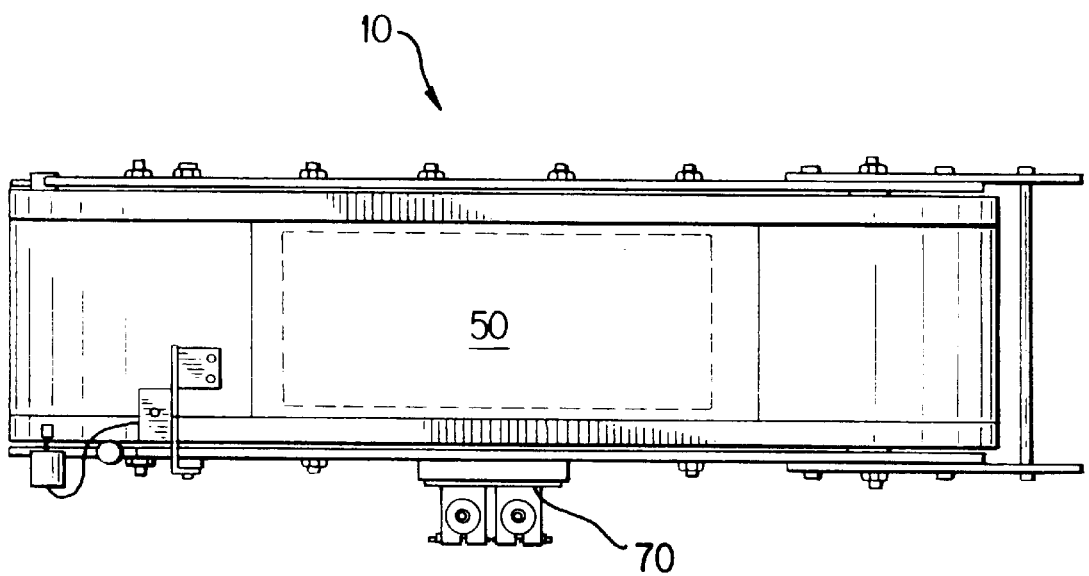
Figure 9:
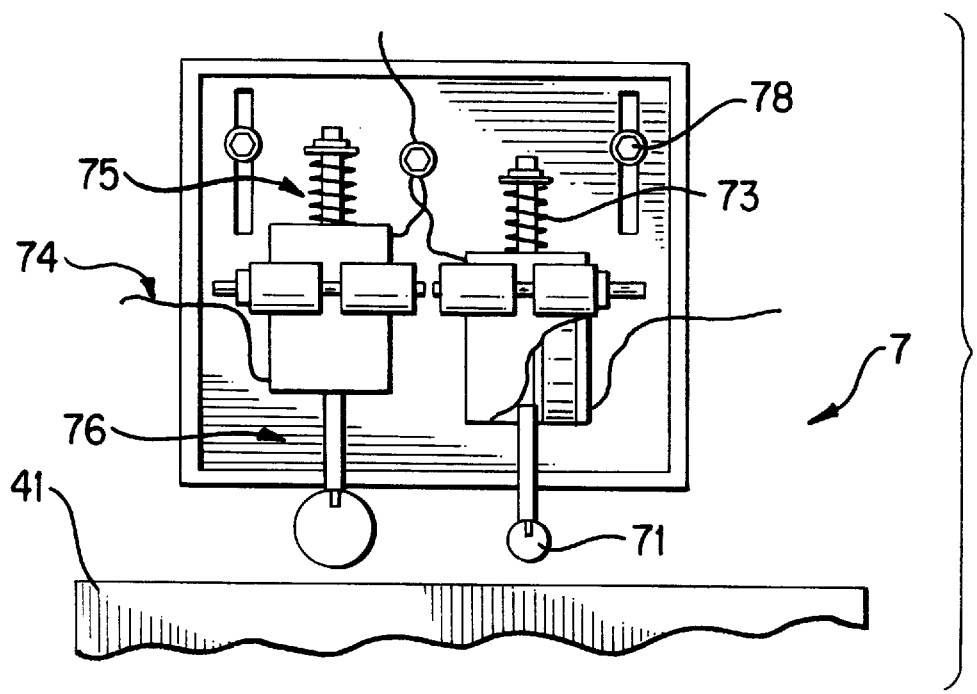
FIGS. 9 & 10 show a top and side view of the impact device.
Figure 10:
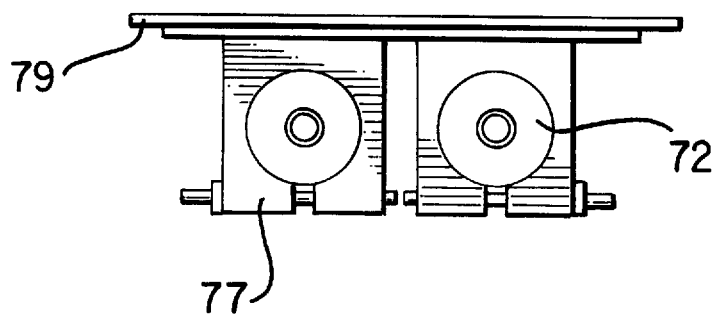

An alternative application of the ultrasonic scanning carriage 10 includes use of impact-echo resonant testing in conjunction with UPE testing. FIGS. 7 & 8 show a side and top view of the carriage with the additional optional feature of a solenoid impact device 70 for performing impact-echo resonant testing with carriage 10. FIGS. 9 & 10 show a top and side view of the solenoid impact device 70 which is mounted to carriage 10 through rubber mounting pads 79. The impact device 70 generates longitudinal resonant frequencies in a test specimen. The coupling technique of the ultrasonic scanning carriage 10 can then be used to receive the resulting resonating acoustical energy from the test specimen. Because small diameter impactors 71 are required for resonating thin specimens and larger diameters impactors are desired for resonating thicker specimens, many of these impacting devices may be excited sequentially to provide high resolution testing results over a wide range of specimen depths. For example, a large impactor 71 would produce the best test signal for a deep interface such as the backwall, while a small impactor would be needed to produce a test signal which revealed a shallow interface such as a delamination near the test surface. In addition to electromechanical impactors 71 such as solenoids, pneumatic sources such as a BB pistol can be used to create the desired impact stimulus.

The operation of the impact-echo test using carriage 10 requires use of the output from the rotary pulse encoder 32 which would alternately trigger different impactors 71. A current amplifier is used to connect a low impedance solenoid 72 through solenoid leads 74 to a function generator or equivalent circuit. The function generator creates a single square-wave electrical pulse of variable width whose amplitude goes from zero to a positive voltage and then back to zero. The width of this pulse can be adjusted during system setup so that the impactor 71 is propelled by momentum and not by electromagnetic force when specimen 41 contact is made. This is desired so that a known force-time energy function is applied to the specimen 41.

The amplitude of this square-pulse can be varied to control the electromagnetic force applied. The spring 73 above the solenoid 72 would then pull the impactor 71 back into its initial resting position as shown in FIG. 9. Sliders 77 and adjusters 78 allow adjustment so that the optimum impactor 71 distance from the surface 41 can be defined. The shaft 75 to which the impactor 41 is mounted should be non-ferrous and acoustically impedance mismatched to the impactor in region 76. Plastic is an example of one such material. The shaft in region 75 should be either ferrous or magnetic so as to be propelled toward the specimen when the solenoid 72 is activated.

Another alternative feature of the invention includes varying the angle of the directed acoustical beam as the ultrasonic scanning carriage 10 moves. This feature would provide additional test information and increase the data acquisition robustness. Electronic beam steering techniques is one way of accomplishing this where transducer's 12 mosaic pattern 21 is broken into smaller elements 25. These elements 25 would be individually excited by delayed pulses. The exact beam pattern and direction are dependent on the specific electrical pulse delays used. Another way includes use of a mechanical cam which would raise and lower the transducers 12 as the carriage 10 moves. Also, individual signals from the peiezoelectric elements in the transducer receiver's mosaic design can be digitized. These signals can then be used by signal processing techniques that can enhance echo detection and classification.

While this invention has been described in terms of a preferred embodiment, it is understood that it is capable of further modification and adaptation of the invention following in general the principle of the invention and including such departures from the present disclosure as come within the known or customary practice in the art to which the invention pertains and may be applied to the central features set forth, and fall within the scope of the invention and the appended claims.

We claim:

1. Apparatus for simultaneously transporting acoustical testing mechanisms across the surface of a solid specimen while analyzing the condition of the interior of that specimen by acoustic waves traveling within the specimen and reflecting from surface boundaries within the specimen comprising:

an assembly within a frame for acoustically communicating with the specimen including at least a single pair of planar type acoustical communicating elements and an acoustic isolation device placed between the pair of elements that is in contact with the specimen surface, a fluid sealing roller-traction means including a pair of outer belts and front and back rollers for rolling on the external surface of the specimen that is attached to the frame for allowing movement in a direction of the frame over the surface of the specimen with a relatively constant spacing therefrom, a pulse encoder means for actuation of the acoustical communicating assembly that is mechanically coupled to the roller-traction means, an acoustical-transmissive fluid maintained and sealed within a base portion of the fluid sealing roller-traction means between said belts and roller and a bottom portion of the at least a single pair of planar acoustical communicating elements and the specimen surface such that said fluid is carried across the specimen, and means for attaching the assembly to the frame to suspend the assembly above the specimen surface as the frame is motivated over the specimen surface for establishing acoustical communication with the interior of the specimen, the attaching means including means for physical adjustment of each of the acoustical communicating elements.

2. Apparatus in accordance with claim 1 wherein the acoustical communicating elements are ultrasonic planar wavefront transducers, each transducer comprising:

a solid acoustic impedance matching wedge of planar construction with a first planar face for emplacement on the specimen surface, a quarter wavelength impedance matching plate is attached to a second face opposite to the first planar face, at least one piezoelectric component with an electrode is attached to an opposite anterior side of the quarter wavelength impedance matching plate, and wherein each at least one piezoelectric component and each transducer are encased in a protective waterproof covering component.

3. Apparatus in accordance with claim 2 wherein the specimen is concrete, each wedge is made of granite, each quarter wavelength impedance matching plate is short-flint glass and each at least one piezoelectric component is made of low quality factor lead metaniobate forming several individual elements in a mosaic pattern on the corresponding matching plate.

4. Apparatus in accordance with claim 1 wherein the acoustical communicating assembly further includes means for impacting the surface of the specimen.

5. Apparatus in accordance with claim 4 wherein the impacting means includes means responsive to movement of the frame for actuating the impacting means after a predetermined amount of movement has occurred between the frame and the specimen.

6. Apparatus in accordance with claim 5 wherein the impacting means includes a shaft, means mounting the shaft for movement in a direction near the surface of the specimen, and means coupling the pulse encoder for causing the shaft to impact the specimen surface in response to movement of the roller-traction means over the specimen surface for a predetermined distance.

7. Apparatus in accordance with claim 6 wherein the shaft mounting means includes means for biasing the shaft in a direction towards the specimen surface for applying impacting force to the shaft after the shaft is activated in response to signals from the encoder means.

8. Apparatus in accordance with claim 7 which includes a plurality of the impacting means attached to the frame.

9. Apparatus in accordance with claim 8 wherein shafts of the plurality of impacting means are released at different points of travel of the roller-traction means over the specimen surface.

10. Apparatus in accordance with claim 4 wherein the impacting means includes a solenoid means and means for selectively introducing an energizing signal to the solenoid means.

11. Apparatus in accordance with claim 1 wherein the assembly further includes a spring loaded bristle brush device that is immersed in the fluid that contacts the specimen surface.

12. Apparatus in accordance with claim 1 wherein the acoustical communicating assembly further includes wave trapping sponges attached to the means for attaching the assembly to the frame, the sponges are immersed in the fluid.

13. Apparatus for simultaneously transporting acoustical testing mechanisms across the surface of a concrete specimen while analyzing the condition of the interior of that specimen by acoustic waves traveling within the concrete specimen and reflecting from surface boundaries within the concrete specimen comprising:

an assembly within a frame for acoustically communicating with the specimen including at least a single pair of planar type acoustical communicating elements and an isolation device such elements are ultrasonic planar wavefront transducers that include:

a solid acoustic impedance matching granite wedge of planar construction with a first planar face for emplacement on the specimen surface, a quarter wavelength impedance matching short-flint glass plate is attached to a second face opposite to the first planar face, at least one piezoelectric component made of low quality factor lead metaniobate forming several individual elements in a mosaic pattern with an electrode is attached to an opposite anterior side of the glass plate, wherein each at least one piezoelectric component and each transducer is encased in a protective waterproof covering component, a fluid sealing roller-traction means including a pair of outer belts and front and back rollers for rolling on the external surface of the specimen that is attached to the frame for allowing movement in a direction of the frame over the surface of the specimen with a relatively constant spacing therefrom, a pulse encoder means for actuation of the acoustical communicating assembly that is mechanically coupled to the roller-traction means, an acoustical transmissive fluid maintained and sealed within a base portion of the fluid sealing roller-traction means between said belts and roller and a bottom portion of the at least a single pair of planar acoustical communicating elements and the specimen surface such that said fluid carried across and the specimen, means for attaching the assembly to the frame to suspend the assembly above the specimen surface as the frame is motivated over the specimen surface for establishing acoustical communication with the interior of the specimen, the attaching means including means for physical adjustment of each of the acoustical communicating elements, and a spring loaded bristle brush device is attached to the assembly that is immersed in the fluid that contacts the specimen surface.

14. Apparatus in accordance with claim 13 wherein the acoustical communicating assembly further includes wave trapping sponges attached to the means for attaching the assembly to the frame, the sponges are immersed in the fluid.

15. Apparatus in accordance with claim 13 wherein the acoustical communicating assembly further includes means for impacting the surface of the specimen.

* * * * *

UNITED STATES PATENT AND TRADEMARK OFFICE
CERTIFICATE OF CORRECTION

PATENT NO. : 5,814,731
DATED : September 29, 1998
INVENTOR(S) : Alton Michel Alexander, et al It is certified that error appears in the above-identified patent and that said Letters Patent is hereby corrected as shown below:

On the title page item [76], "Haskin" should read --Haskins--.

Signed and Sealed this

Sixteenth Day of March, 1999

Attest:

Q. TODD DICKINSON

*Attesting Officer*    *Acting Commissioner of Patents and Trademarks*